United States Patent [19]
Reich

[11] Patent Number: 4,469,442
[45] Date of Patent: Sep. 4, 1984

[54] DETECTING IRREGULARITIES IN A COATING ON A SUBSTRATE

[75] Inventor: Frederich R. Reich, Richland, Wash.

[73] Assignee: Japan Crown Cork Co., Ltd., Japan

[21] Appl. No.: 338,384

[22] Filed: Jan. 11, 1982

[51] Int. Cl.³ .............................................. G01N 21/21
[52] U.S. Cl. .................................... 356/364; 356/237; 250/225
[58] Field of Search ............... 356/237, 364, 365, 366, 356/367, 369, 429, 430, 431; 250/225

[56] References Cited

U.S. PATENT DOCUMENTS 4,342,515  8/1982  Akiba .................................. 356/369
4,381,151  4/1983  Smith .................................. 356/369

Primary Examiner—R. A. Rosenberger
Attorney, Agent, or Firm—Beveridge, DeGrandi & Kline

[57] ABSTRACT

Irregularities in a coating on a substrate in which the coating includes optical scattering centers can be detected by irradiating the coating with polarized light and examining light from the coating through a filter which removes light having the same polarization as the initial beam. Light scattered by the optical scattering centers is transmitted through the filter, while specularly reflected light from the top surface of the coating, from the substrate exposed by gaps in the coating, or reflected by alien material on the coating is filtered out. As a result irregularities can be detected as intensity minima of the transmitted radiation.

33 Claims, 14 Drawing Figures

DETECTING IRREGULARITIES IN A COATING ON A SUBSTRATE

BACKGROUND OF THE INVENTION

The present invention relates to a method and apparatus for detecting irregularities in a coating on a substrate. More particularly, the present invention relates to the inspection of painted or lacquered surfaces, such as surfaces on container closures including metal screw and lug cap components. Such inspection is performed to detect physical damage and the presence of contamination.

Currently in the container closures production process, considerable effort is expended in inspecting each closure for the presence of surface coating defects and contaminants. The coatings generally include a transparent carrier and pigment particles which scatter incident light. Typical of such coatings are enamels, latex paints, epoxy coatings and lacquers, among others. These can generally be called solid solutions and mixtures.

Coating defects can include the presence of alien materials such as stains and residual sealing materials, physical damage from scratching or abrasion, and pin holes. Cosmetic and functional properties of the closure can be adversely affected by alien material or by flaws in the protective surface. Damage to the coating may expose the underlying closure material to corrosion which may lead the closure to fail.

To maintain high product quality, it is necessary to separate defective caps from good caps. Because some of these defects, such as pin holes, are extremely small, naked eye inspection is not only inefficient, but is also relatively ineffective. Closures also generally contain some embossed structure which must be ignored by an inspector. Optical techniques that rely on the contrast difference between defective and good cap areas can misread these embossed structures, since they also produce contrast differences.

Thus, there is a need for a simple, inexpensive, reliable method and apparatus for inspecting coatings on a substrate to detect irregularities.

The use of polarized light to aid in inspections of surfaces is not, per se, new. For instance, U.S. Pat. No. 2,947,212 to R. C. Woods discloses a method for inspecting striated sheet metal moving parallel to the striations in which the metal surface is exposed to polarized light. The striations, consisting of microscopic peaks and valleys in the metal surface, cause non-specular reflection into a detector. The reflected light is filtered to pass only the polarized light. Variations in the intensity of the reflected beam represent variations in the striation.

In U.S. Pat. No. 3,904,293 to Gee, polarized light is beamed at a road surface. The reflected light has a certain degree of depolarization indicative of the surface texture of the road.

In U.S. Pat. No. 4,015,127 to Sharkins, a beam of non-polarized infrared radiation is directed at a coating on a metal substrate, at Brewster's Angle, so that the beam is plane-polarized if reflected from the top surface of the coating. Radiation not so reflected from the top surface of the coating penetrates and is partially absorbed by the coating and partially reflected at the interface of the coating and substrate. The polarized light is filtered out of the reflected beam so that the intensity of the portion of the incident beam penetrating the coating can be monitored without including the reflections from the top surface. The thickness of the coating can be determined by correlating it with the attenuation in beam intensity caused by absorption in the coating. Sharkins also discloses other combinations of polarizing filters and applications of Brewster's Angle to eliminate the unwanted polarized reflected beam.

None of these prior patents disclose the simple method or apparatus of the present invention for ascertaining the presence of irregularities in a coating. In particular, none of these patents discloses detection of surface contaminants while disregarding desirable embossing.

SUMMARY OF THE INVENTION

The present invention provides a method for ascertaining the presence of irregularities in a coating on a substrate in which the coating includes optical scattering centers including the steps of irradiating the coating with a polarized electromagnetic radiation such that radiation which may be incident on the substrate is reflected with its original polarization while radiation incident on the scattering centers is scattered, thereby depolarizing the scattered radiation, receiving radiation reflected and scattered from the coating, transmitting the received radiation through a means for removing the reflected polarized radiation, and analyzing the transmitted radiation to ascertain the presence of the irregularities by recognizing intensity minima of the transmitted radiation.

Preferably, the means for removing the reflected polarized radiation is a polarizing filter having a pass-axis substantially perpendicular to the axis of the electric field vector of the reflected polarized radiation.

In one embodiment the analyzing step includes measuring the intensity of the transmitted radiation and correlating the measured intensity with different areas of the coating.

In another embodiment the irradiating step includes scanning the coating with the polarized radiation in a predetermined pattern. In this embodiment the analyzing step can include measuring the intensity of the transmitted radiation and ascertaining the presence of the irregularities in the coating by recognizing discontinuous variations in the measured intensity as the coating is scanned. Optionally the irradiating step can include irradiating the coating with laser emissions and the transmitting step can include filtering the received radiation to pass only radiation in the frequency band of the laser emissions. Furthermore, the transmitting step can include diffusing the transmitted radiation.

The coating can be scanned in any of a large number of patterns including a spiral pattern, a raster scan pattern, or a polar scan pattern about the center of the coating. No matter which pattern is used, the analyzing step may include correlating the measured intensity with the predetermined scan pattern. Even if the substrate is non-planar, the analyzing step does not identify non-planar portions of the substrate as irregularities.

In another embodiment, the coating is substantially continuously and substantially uniformly irradiated with polarized electromagnetic radiation. In this embodiment, the analyzing step includes introducing the transmitted radiation into a video camera. Then the analyzing step further includes detecting the input signal of the video camera to determine rapid video signal level changes indicative of irregularities in the coating.

The invention also includes apparatus adapted to perform the methods as hereinabove described.

BRIEF DESCRIPTION OF THE DRAWINGS

The invention will be better understood from a reading of the following description in conjunction with a study of the drawings in which.

DETAILED DESCRIPTION OF THE PREFERRED EMBODIMENTS

Figure 1:
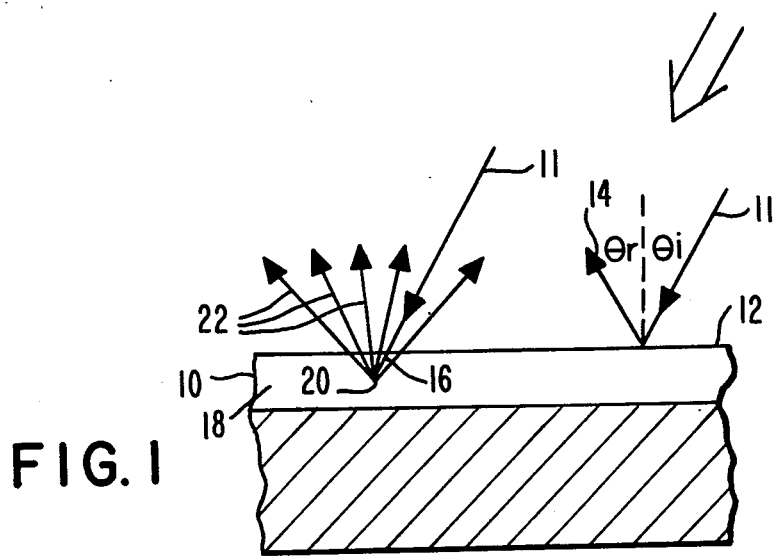
FIGS. 1 and 2 are schematic sectional views of a substrate exposed to polarized light.

The present invention makes use of the scattering and depolarization of light of an incident polarized light beam to assess the acceptability of a painted or lacquered surface. The depolarization of the incident light is produced by the interaction of the pigment particles in the paint or lacquer coating 10 with an incident polarized light beam 11, which is at a nonzero angle with respect to the principal plane of the substrate 26, as illustrated in FIG. 1. When a beam of polarized light is incident on the coating 10, a portion of the light 14 will be reflected at the initial surface 12 while the remaining light 16 penetrates into the coating where it interacts with the pigment medium. Since the lacquer or paint carrier base of coating 10 is generally clear, its effects on the light beam can be largely ignored as it only produces a slight absorption of the light beam.

The pigment particles 20, however, severely affect the light beam by selective absorption of certain wavelength bands resulting in the color aspects of the paint. More important to this invention, however, the pigment particles scatter the incident light. In the scattering process light energy is absorbed and then reradiated as spherical waves from each scattering center. Because of the size of particle 20 relative to the incident light wavelength, each particle contains many potential scattering centers. The net result, as illustrated in FIG. 1, is the alteration of the direction and state of polarization of the beam radiated from these scattering centers, from those of the incident beam.

Figure 2:
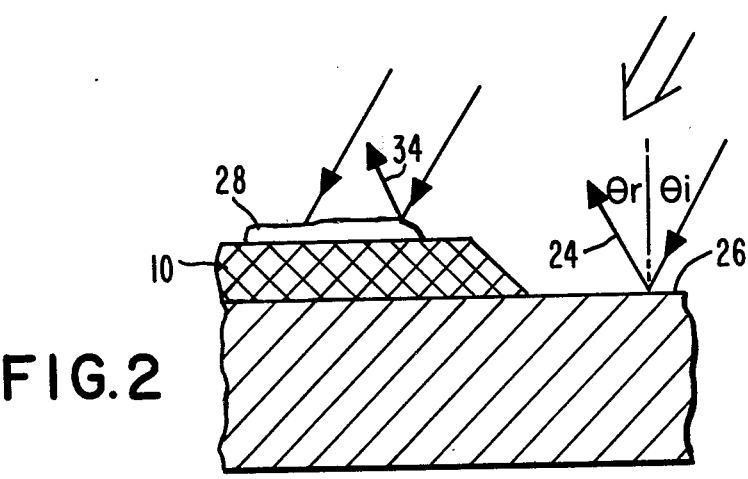

The portion of the optical beam which is reflected from the initial surface 12 of the paint depicted in FIG. 1, retains the initial beam polarization, as does any portion 24 reflected from the exposed underlying metal substrate 26 depicted in FIG. 2. Both of these specularly reflected portions follow the rules of optical reflection in which the angle of incidence, $\theta i$, equals the angle of reflection $\theta r$. Any alien material 28 shields an area of coating 10 from the incident light and either absorbs the light or reflects it, as reflected light ray 34, with the same polarization as the incident optical beam. Since the light beam does not penetrate the opaque alien material, it is not scattered, but is either absorbed or reflected.

Thus the light coming from the surface 10 includes reflected light rays 14, 24, and 34 and scattered light rays 22. Light is generally visible from all parts of the closure surface due to the broad angle of the scattering, although the reflected light rays 14, 24 and 34 are concentrated at angle $\theta r$.

Figure 3:
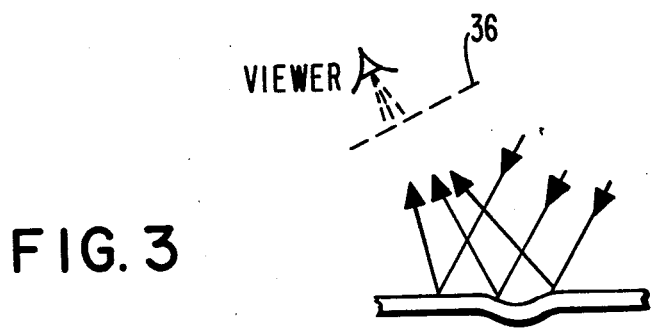
FIG. 3 is a schematic, fragmentary sectional view of an embossed structure exposed to polarized light.

Scattered beam 22 does not have the same polarization as the incident beam, but reflected beams 14, 24 and 34 do. If the surface is viewed through a polarizing element 36, as depicted in FIG. 3, the polarizing element can be rotated until the polarized reflected light beams 14, 24 and 34 are blocked. In this position, the pass-axis of the polarizing element is perpendicular to the axis of the electric field vector of the incident polarized optical beam. As viewed through the polarizing element, only the surface areas adequately covered with the scattering pigment are bright. Irregularities in the coated surface, such as those covered with a contaminant material, or having pin holes or scratches in the coating, appear dark. Other areas in the coating appear bright because of the broad angle of the radiation of the scattered light. This is true of curved areas of the coating on non-planar portions of the substrate as well, as shown in FIG. 3. This is an important property since most closures contain some embossed structures to enhance the cap strength and to support the cap liner for closure sealing.

Thus all of the cap surface, including the embossing, appears bright to the viewer, unless the protective lacquer or paint has been covered by some alien material or has been damaged by a pin hole, scratching or abrasion or other defect.

In connection with inspecting container closures, the present invention is useful in detecting the presence of contaminants on the coating or holes or scratches in the coating. A normal, properly coated cap surface scatters and highly depolarizes an incident polarized optical beam, while defective areas reflect or absorb this light with smaller change in the optical polarization.

Figure 4:
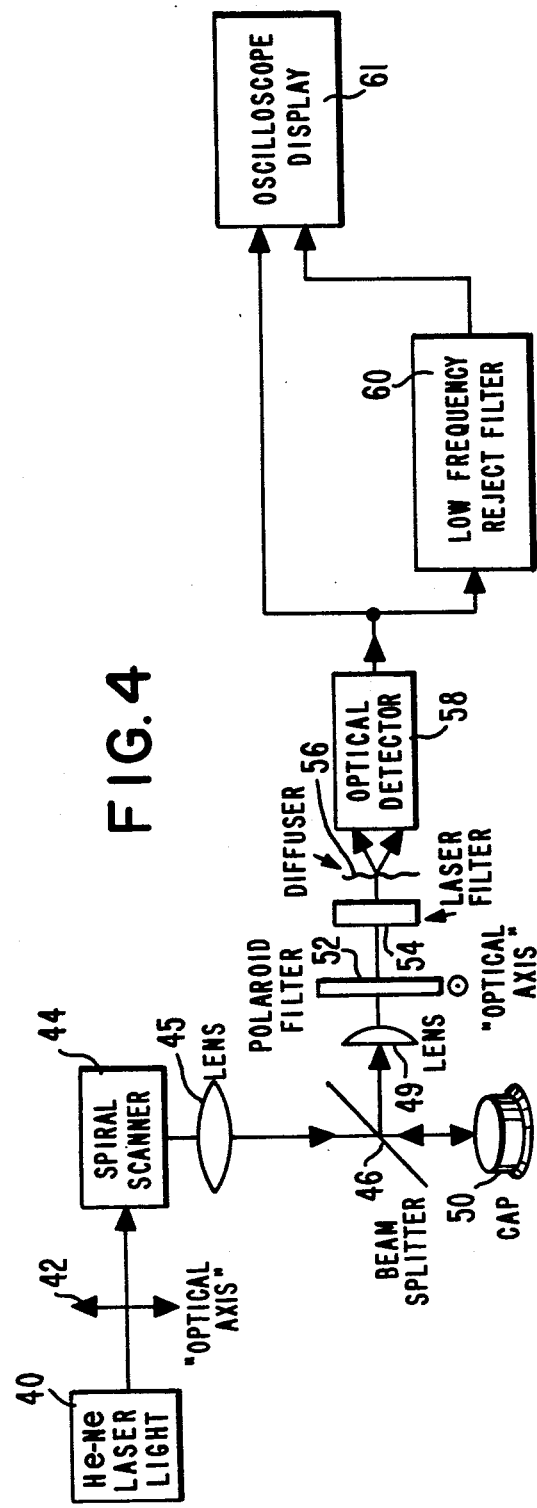
FIG. 4 is a schematic view of an apparatus according to one embodiment of the invention.

One embodiment of the invention using these optical principles is shown in FIG. 4. However, from the following description of a presently preferred embodiment, other embodiments implementing these optical principles will be apparent to those of ordinary skill, and the specific embodiments disclosed herein are not limitative but illustrative, although at present preferred.

The illumination source 40 in FIG. 4 is a polarized Helium-Neon laser. Other possible sources include unpolarized lasers, tungsten filament lamps and arc lamps, with a subsequent polarizing element to produce a polarized optical beam having a defined optical axis. As shown in FIG. 4 the optical axis is vertical in the plane of the page as designated by arrow 42. Various wavelength bands for the illumination source can be used, although visible light is preferred as being especially convenient.

The output beam of laser 40 is subjected to a scanner, such as a spiral scanner 44. Scanning system 44 scans the polarized beam over the area of the cap. The scanning beam passes through lens 45 and beam splitter 46 to cap 50. The reflected radiation from cap 50 is reflected by beam splitter 46 through collecting lens 49, polarizing filter 52, laser filter 54, and diffuser 56 to optical detector 58. Beam splitter 46 can be a conventional, partially silvered (chrome or aluminum) glass plate with no polarization sensitivity, or a special multilayer dielective coating that selectively reflects or transmits light according to its polarization direction. Preferably the optical axis of the light from source 40 is either parallel or perpendicular to the plane of beam splitter 46 to prevent any interference with the polarization of the transmitted light.

The polarization of the specularly reflected portion of the light from cap 50 is the same as that of the original source 40. The optical pass axis of filter 52 is into the paper and is perpendicular to the optical axis 42 of the polarized component of the reflected light. Consequently filter 52 blocks the reflected portions of the beam, allowing the non-polarized, scattered portion to pass.

Laser filter 54 is "tuned" to pass a narrow spectral band around the laser wavelength and to block optical detector 58 from ambient light, thereby enhancing the detector signal-to-noise ratio. Detector 58 can be of the type that converts the light to electrical signals, which can be applied to ocilloscope 61 either directly or through high pass filter 60. The optical diffuser 56, which can be a simple sheet of frosted glass or Mylar plastic film, distributes the incoming light uniformly over the detector face to produce a more uniform signal regardless of the portion of the total cap area being scanned. Due to the elimination of polarized components by filter 52, detector 58 receives light only from the good surface areas of cap 50. Since the optical scatter from the cap is distributed over a large solid angle, the detector receives a substantially uniform response from all good areas of the cap, including the embossed areas where the cap surface is not smooth or flat. Without the polarizing filter 52 the non-flat cap areas could not be distinguished from the defect areas.

Figure 5:
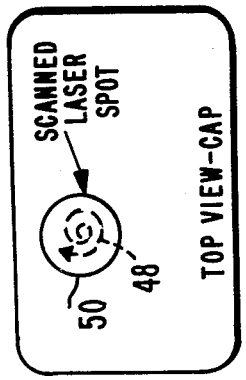
FIG. 5 is a schematic view of the top of a cap showing one possible scanning pattern.

FIG. 5 schematically depicts the spiral scanning pattern, the beam traversing path 48 on the surface of cap 50. Although a spiral scan system is shown in FIGS. 4 and 5, there are other equally effective scanning patterns, such as an x-y raster scan or a polar scan which rotates a line scan about the center of the cap. The scanner illuminates at one time or another all of the cap surface area for the detection of surface defects or contaminants.

The length of time required to scan a cap, of course, is related to the sizes of the scanning beam and cap and the rate of travel of the beam. The size of the beam is selected according to the preference for brief scanning times or higher resolution. It will be apparent that there is a minimum beam size required to generate sufficiently strong output signals. Typically the beam size can be 0.005 to 0.01 inch in diameter, with scanning times on the order of 0.1 to 0.25 sec. per cap.

As will be apparent, as long as the beam is scanning good areas of the cap, a non-polarized beam of a relatively uniform level of intensity will be scattered and detected. When the scanning incident beam encounters an irregularity, either very little light, or mostly only polarized light will be reflected. Either result will be detected as a relative minimum in the intensity in detector 58. Thus such minima can be recognized as irregularities.

Figure 6:
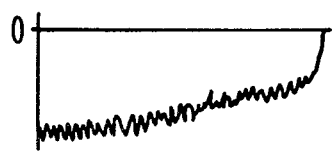
FIGS. 6 through 13 depict traces of signals generated by the embodiment of FIG. 4 under varying conditions.
Figure 7:
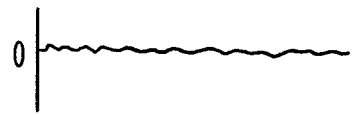

FIGS. 6 and 7 illustrate the signal produced by scanning a good cap.

Figure 8:
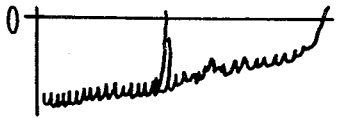
Figure 9:
Figure 10:
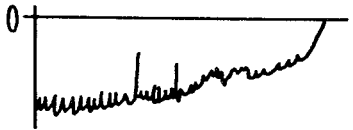
Figure 11:
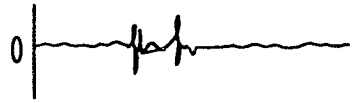
Figure 12:
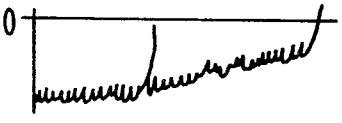
Figure 13:
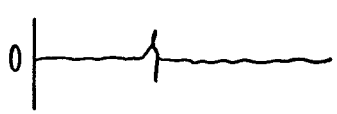

FIGS. 8 and 9 illustrate the signal response produced by a scratch. FIGS. 10 and 11, and FIGS. 12 and 13 illustrate the signal response of alien material contaminants and of a pin hole respectively.

FIGS. 6, 8, 10 and 12 show typical signals from the optical detector 58 and FIGS. 7, 9, 11 and 13 show the same signals respectively after being filtered by high frequency pass filter 60 to which the output of detector 58 is applied. With the spiral scan, slight variations in the scatter from the cap surface produce a low frequency ac signal, with a dc signal level reduction as the perimeter area of a cap is scanned. This low frequency can be removed by high frequency pass filtering, leaving only the defect signal. For the detector signals illustrated in FIGS. 6, 8, 10 and 12, the dc decrease in signal level produces an upward trace motion. As the laser beam scans off the edge of the cap, the signal approaches zero. With the high frequency pass processing as seen in FIGS. 7, 9, 11 and 13, the low frequency ac and dc components are removed, leaving only the high frequency flaw signal which may be applied to a comparator for an automatic indication of a defective cap surface.

Figure 14:
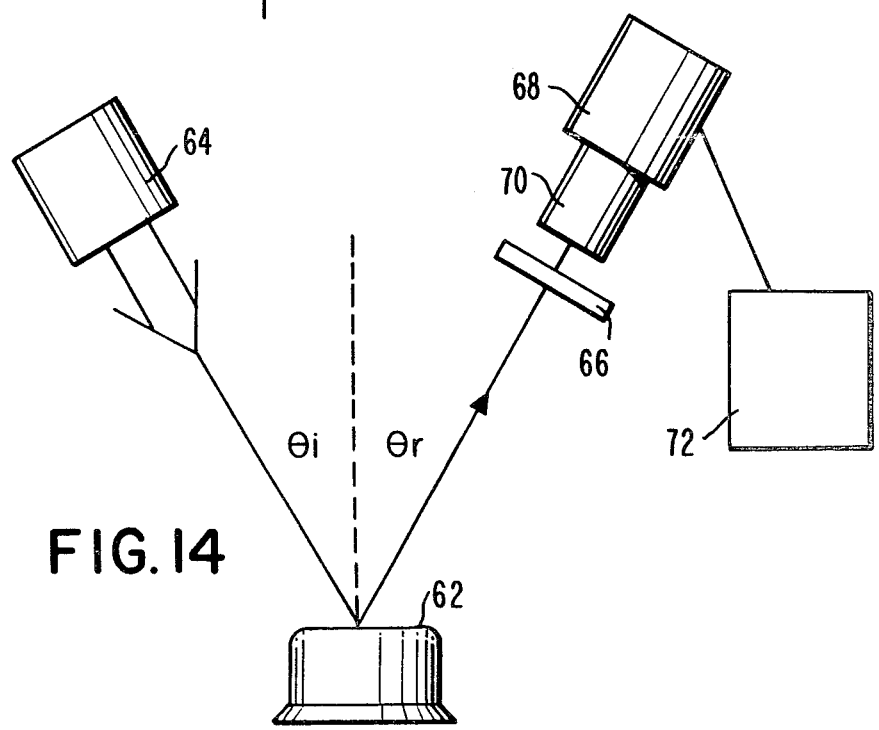
FIG. 14 is a schematic view of an apparatus according to a second embodiment of the invention.

There are other methods of implementing the basic principles of the optical depolarization for inspection, including the use of other flying spot scanning methods and the use of video based camera systems. One such video system is illustrated in FIG. 14. The entire cap 62 is illuminated by a uniform polarized light source 64. As before, the incident light is scattered and depolarized if it is incident on the scattering centers in the pigment of the coating on the cap. Light incident on contamination on the coating or scratches or pin holes in the substrate is either absorbed or specularly reflected, retaining its original polarization. Similarly, the specular reflection from the top surface of the coating retains its original polarization. The polarized components of light along angle $\theta r$ are filtered out by polarizing element 66 leaving only the depolarized light from the scattering centers in the coating to be transmitted through element 66 to video camera 68.

Video camera 68 operates in a normal television mode in which the light through lens 70 is incident on a photosensitive surface. The surface generates electrical charges corresponding to the amount of light falling thereon, and the camera produces a sequence of signals corresponding to various portions of the surface as it is addressed in a predetermined sequence. For a completely uniform image, the output signal has a constant level, but when the image has a discontinuity the signal level changes rapidly. Such a discontinuity could be caused by a pin hole, scratch, contaminant, or other defect on a cap. The resulting rapid change in the level of the output signal from video camera 68 is thus indicative of a defective cap.

Discontinuities caused by cap edges can be disregarded if the caps inspected are always presented in the same position, with the same background, so that they all present identical edge discontinuities. Signal processing module 72, to which the output of video camera 68 is applied, can be programmed to disregard such expected edge discontinuity signals in a manner which will be apparent to those in the art.

What is claimed is:

1. A method of detecting irregularities in a coating on a substrate having a principal plane, which coating includes optical scattering centers, said method comprising the steps of:

directing polarized electromagnetic radiation onto the coating at a nonzero angle to the principal plane such that the radiation incident on the substrate is reflected with its original polarization and radiation incident on the scattering centers is scattered, thereby depolarizing the scattered radiation;

transmitting the reflected and scattered radiation through an element for removing the reflected radiation;

receiving the transmitted scattered radiation;

analyzing the received radiation to detect the presence of irregularities in the coating by detecting intensity minima of the transmitted radiation.

2. A method as claimed in claim 1 wherein said reflected radiation is removed by passing the transmitted and reflected radiation through a polarizing filter having a pass-axis substantially perpendicular to the axis of the electric field vector of the reflected radiation.

3. A method as claimed in claim 1 wherein said directing step includes scanning the coating with the polarized radiation in a predetermined pattern.

4. A method as claimed in claim 3 wherein said analyzing step includes measuring the intensity of the transmitted radiation and ascertaining the presence or irregularities by detecting discontinuous variations in the measured intensity as the coating is scanned.

5. A method as claimed in claim 4 wherein said transmitting step includes diffusing the transmitted radiation.

6. A method as claimed in claim 5 wherein said pattern is a spiral pattern.

7. A method as claimed in claim 5 wherein said pattern is a raster scan pattern.

8. A method as claimed in claim 5 wherein said pattern is a polar scan pattern.

9. A method as claimed in any one of claims 6, 7, or 8 wherein said substrate has a non-planar portion the scanning of which results in only a continuous variation in the measured intensity in said analyzing step.

10. A method as claimed in claim 3 wherein said directing step includes irradiating the coating with laser emissions and said transmitting step includes filtering the received radiation to pass only radiation in the frequency band of said laser emissions.

11. A method as claimed in claim 1 wherein the directing step comprises substantially continuously and substantially uniformly irradiating said coating with the polarized electromagnetic radiation.

12. A method as claimed in claim 11 wherein said analyzing step comprises introducing the transmitted radiation into a video camera.

13. A method as claimed in claim 12 wherein said analyzing step further includes detecting the output signal of said video camera to determine rapid video signal level changes indicative of irregularities.

14. A method as claimed in claim 1 wherein said directing step includes irradiating said coating with said polarized electromagnetic radiation at an angle of incidence, thereby causing said reflected radiation to be reflected at an angle of reflection and wherein said transmitting step includes transmitting said radiation reflected at said angle of reflection through said element for removing the reflected radiation.

15. A method as claimed in claim 1 wherein said electromagnetic radiation is visible light.

16. A method as claimed in claim 1 wherein said directing step includes irradiating contaminants on said coating such that radiation incident on said contaminants is reflected with its original polarization and wherein said transmitting step includes transmitting the radiation reflected from said contaminants through the element for removing the reflected radiation, thereby removing the radiation reflected from said contaminants.

17. A method as claimed in claim 1 in which the polarized electromagnetic radiation is directed onto the coating substantially perpendicularly to the principal plane.

18. Apparatus for ascertaining the presence of irregularities in a coating on a substrate having a principal plane, which coating includes optical scattering centers, said apparatus comprising:

means for directing polarized electromagnetic radiation onto the coating at a nonzero angle to the principal plane such that radiation incident on the substrate is reflected with its original polarization and radiation incident on the scattering centers is scattered, thereby depolarizing the scattered radiation;

means for removing the reflected polarized radiation from reflected and scattered radiation while transmitting the unpolarized scattered radiation;

means for receiving the transmitted scattered radiation;

means for analyzing the received radiation to detect the presence of irregularities in the coating by detecting intensity minima of the transmitted radiation.

19. An apparatus as claimed in claim 18 wherein said means removing the reflected polarized radiation is a polarizing filter having a pass-axis substantially perpendicular to the axis of the electric field vector of the polarized reflected radiation.

20. An apparatus as claimed in claim 18 wherein said directing means includes means for scanning the coating with polarized radiation in a predetermined pattern.

21. An apparatus as claimed in claim 20 wherein said analyzing means includes means for measuring the intensity of the transmitted radiation and ascertaining the presence of the irregularities by detecting discontinuous variations in the measured intensity as the coating is scanned.

22. An apparatus as claimed in claim 20 wherein said directing means includes means for irradiating the coating with laser emissions and said apparatus includes means for filtering the received radiation to pass only radiation in a frequency band approximating the frequency of said laser emissions.

23. An apparatus as claimed in claim 22 including means for diffusing said received radiation.

24. An apparatus as claimed in claim 20 wherein said pattern is a spiral pattern.

25. An apparatus as claimed in claim 20 wherein said pattern is a raster scan pattern.

26. An apparatus as claimed in claim 20 wherein said pattern is a polar scan.

27. An apparatus as claimed in any one of claims 24, 25 or 26 wherein the substrate has a non-planar portion, the scanning of which results in only a continuous variation in the intensity as detected by said analyzing means.

28. An apparatus as claimed in claim 18 wherein said directing means substantially continuously and substantially uniformly irradiates the coating with polarized electromagnetic radiation.

29. An apparatus as claimed in claim 28 wherein said analyzing means comprises a video camera.

30. An apparatus as claimed in claim 29 wherein said analyzing means further includes means for detecting the output signal of said video camera to determine rapid video signal level changes indicative of said irregularities.

31. An apparatus as claimed in claim 18 wherein said directing means irradiates said coating at an angle of incidence thereby causing said reflected radiation to be reflected at an angle of reflection, and wherein said means for removing the reflected polarized radiation is oriented at said angle of reflection.

32. An apparatus as claimed in claim 18 wherein said directing means irradiates said coating with visible light.

33. An apparatus as claimed in claim 17 in which said means for directing electromagnetic radiation directs the radiation onto the coating substantially perpendicularly to the principal plane.

* * * * *